(12) United States Patent
Demas et al.

(10) Patent No.: US 7,749,765 B2
(45) Date of Patent: Jul. 6, 2010

(54) QUANTITATIVE DETECTION OF LEAD IN WATER

(75) Inventors: James N. Demas, Charlottesville, VA (US); Wenying Xu, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 195 days.

(21) Appl. No.: 11/997,630

(22) PCT Filed: Aug. 3, 2006

(86) PCT No.: PCT/US2006/030372

§ 371 (c)(1),
(2), (4) Date: Feb. 1, 2008

(87) PCT Pub. No.: WO2007/019276

PCT Pub. Date: Feb. 15, 2007

(65) Prior Publication Data

US 2008/0280366 A1     Nov. 13, 2008

Related U.S. Application Data

(60) Provisional application No. 60/705,679, filed on Aug. 4, 2005.

(51) Int. Cl.
*G01N 33/20* (2006.01)
*B01J 13/02* (2006.01)

(52) U.S. Cl. .................... 436/77; 436/73; 436/164; 436/172; 210/638; 210/639; 210/213.3

(58) Field of Classification Search .............. 436/73, 436/74, 76, 77; 356/928
See application file for complete search history.

(56) References Cited

U.S. PATENT DOCUMENTS

| | | | | |
|---|---|---|---|---|
| 4,759,956 A | * | 7/1988 | Amer et al. | 427/213 |
| 5,019,516 A | | 5/1991 | Wiese | |
| 5,100,951 A | | 3/1992 | Fillipo et al. | |
| 5,354,652 A | | 10/1994 | Silbergeld | |
| 5,395,532 A | * | 3/1995 | Chaiko | 210/638 |
| 5,891,736 A | | 4/1999 | Chapoteau et al. | |
| 6,592,991 B1 | * | 7/2003 | Wiesner et al. | 428/404 |
| 2009/0223896 A1 | * | 9/2009 | Diallo | 210/638 |

OTHER PUBLICATIONS

Kavallieratos et al., Fluorescent Sensing and Selective Pb(II) Extraction by a Dansylamide Ion-Exchanger, JACS, 2005, 127, 6514-6515.*
Duan et al., Lead as own luminescent sensor for determination, Spectrochimica Acta Part A, 60, 2004, 1447-1451.*
Singh et al., Electrogenerated chemiluminescence of Pb(II)-bromide complexes, Inorganica Chimica Acta, 2004, 357, 1589-1592.*
Niu et al., Dendrimer-encapsulated metal nanoparticles and their applications to catalysis, 2003, C.R. Chimie, 6, 1049-1059.*

(Continued)

*Primary Examiner*—Krishnan S Menon
*Assistant Examiner*—Allison Gionta
(74) *Attorney, Agent, or Firm*—Rodney L. Sparks (57) ABSTRACT

The present invention provides compositions and methods for extracting, isolating, and measuring lead dissolved in aqueous solutions, including water.

14 Claims, 4 Drawing Sheets

OTHER PUBLICATIONS

Bronich et al., Polymer Micelle with Cross-Linked Ionic Core, 2005, J. Am. Chem. Soc., 2005, 127, 8236-8237.*

Demas et al., Applications of luminescent transition platinum group metal complexes to sensor technology and molecular probes, 2001, Coord. Chem. Rev. 211, 317-351.*

Hongying Duan, et al., "Lead as Own Luminescent Sensor for Determination", Spectra Acta Part A 60, (2004), 1447-1451.

Singh, et al., "Electrogenerated chemiluminescence of Pb(II)-bromide complexes", Inorganic Chimic Acta 2004, 357, 1589-1592.

Kavallieratos, et al., Fluorescent Sensing and Selective Pb(II) Extraction by a Dansylamide Ion-Exchanger, JACS, 2005, 127, 6514-6515.

Niu, et al., Dendrimer-encapsulated metal nanoparticles and their applications to catalysis, 2003, C. R. Chimie, 6, 12049-1059.

Bronich, et al., Polymer Micelle with Cross-Linked Ionic Core, 2005, J. Am. Chem. Soc. 2005, 127, 8236-8237.

Demas, et al., Applications of luminiscent transition platinum group metal complexes to sensor technology and molecular probes, 2001, Coord. Chem. Rev. 211, 317-351.

Clarke, et al., "Lifetime-Based pH Sensor System Based on a Polymer-Supported Ruthenium(II) Complex", Anal. Chem 2000, 72, 3468-3475.

Price, et al., "Polymer-Supported pH Sensors Based on Hydrophobically Bound Luminescent Ruthenium(II) Complexes", Anal Chem 1998, 70, 265-270.

Jones, et al., "The Nature of Pb(II)-Bromide Complexes in Propylene Carbonate", 1982, Polyhedron, 1:2:169-174.

Dutta, et al., "Lead as its Own Sensor", Inorganic Chemistry, 2002, 41:26, 6938-6940.

Gomis, et al., Extractive Fluorimetric Determination of Ultratraces of Lead with Cryptand 2.2.2 and Eosin, 1985, Talanta, 32:9:9215-920.

Weber, et al., "Uber den Nachweis and die Bestimmung des Bleis mit HIfe der Fluoreszenz seiner Chlorokomplexe", Croatica Chemica Acta, CCACAA 47 (1) 51-58 (1975).

Gruijter, W., "Luminescence of Lead Chloride and Lead Bromide Single Crystals: I. The excitation and emission spectra", J. Solid State Chem., 6:1561-162, 1973.

Diaz-Garcia, et al., "Energy transfer-room temperature phosphorescence for the optosensing of transition metal ions", Analytica Chimica Acta 486 (2003), 1-10.

Worsfold, et al., "Integrated luminometer for the determination of trace metals in seawater using fluorescence, phosphorescence and chemiluminescence detection", J of Automated Methods & Management in Chemistry, vol. 24, No. 2, pp. 41-47.

B. San Vicente De La Riva, et al., "Flow Through Luminescence for Heavy Metals Analysis in Sea Water", SPIE vol. 3853, 275-287.

* cited by examiner

QUANTITATIVE DETECTION OF LEAD IN WATER

CROSS REFERENCE TO RELATED APPLICATIONS

This application is a national stage filing of International Application No. PCT/US2006/030372, filed on Aug. 3, 2006, which claims priority under 35 U.S.C. §119(e) to U.S. Provisional Application Ser. No. 60/705,679 filed Aug. 4, 2005, the disclosures of which are incorporated by reference in their entirety herein.

STATEMENT REGARDING FEDERALLY SPONSORED RESEARCH OR DEVELOPMENT

This invention was made with United States Government support under National Science Foundation ("NSF") grant CHE 04-10061. The United States Government therefore has certain rights in the invention.

FIELD OF THE INVENTION

The present invention relates to lead cluster luminescence, radical polymerization, and synthesis and characterization of polymers, and measurement of extracted lead.

BACKGROUND

Lead is a ubiquitous and harmful environmental pollutant. The EPA has established the action level for lead at 72 nM. In certain nonaqueous solvents in the presence of high bromide concentrations (tetrabutylanimonium bromide), lead clusters $(Pb_4Br_{11})^{3-}$ form. These clusters have a moderately efficient luminescence (greenish) that has been proposed as an analytical tool for detecting lead. However, the method is inadequate for direct use with environmental samples because it only works in nonaqueous media and fails in the presence of a small amount of water. This problem would necessitate complex and time consuming pretreatment of samples.

Lead is a toxic metal which can be harmful to human health even at low exposure levels. Lead is sometimes referred to as a cumulative toxin because the lead concentrates in the body. Young children, infants, and fetuses are particularly vulnerable to lead because the physical and behavioral effects of lead occur at lower exposure levels in children than in adults. Overexposure to lead can permanently impair a child's mental and physical development. Comparatively low levels of exposure have been linked to damage to the central and peripheral nervous system, learning disabilities, shorter stature, impaired hearing, and impaired formation and function of blood cells. At its worst, lead poisoning can result in stupor, coma, kidney damage, or severe brain damage.

Lead in drinking water (i.e., potable water) can be a significant contributor to overall exposure to lead, particularly for infants whose diet consists of liquids made with water, such as baby food formula. Consequently, there is a great need to test potable water to determine whether such water contains less than the five parts per billion (ppb) maximum limit proposed by the EPA for public drinking water and to check for less than 10 parts per billion on first draw samples at the point of use. One ppb is equal to one microgram per liter.

Although it is possible to analyze water samples using atomic absorption (i.e. spectroscopic analysis) techniques, such techniques are cumbersome and subject to error due to interferences. For example, the sample must first be prepared in order to convert organic forms of lead to inorganic forms, to minimize organic interferences, and to convert the sample to a suitable solution for analysis. Then the prepared sample is placed into a graphite tube furnace where the sample is slowly evaporated to dryness, charred (ashed) and then atomized. The absorption of hollow cathode radiation during atomization is proportional to the lead concentration.

The atomic absorption method is subject to various disadvantages. For example, it requires the use of an atomic absorption spectrophotometer and a graphite furnace. It also requires a trained operator, a lengthy set-up time, and the equipment required is extremely expensive. Thus, this technique is not suitable for use in the field. Rather it must be used in the laboratory.

Also, the atomic absorption method is subject to various types of interference. The long residence time and high concentrations of the atomized sample in the optical path of the graphite furnace can result in severe physical and chemical interferences. Furnace parameters must be optimized to minimize such effects. Lead analysis can also suffer from severe nonspecific absorption and light scattering caused by matrix components during atomization. Simultaneous background correction must be employed to avoid erroneously high results. Also, if the analyte is not completely volatilized and removed from the furnace during atomization, memory effects will occur, thereby requiring cleaning of the tube by operating the furnace at higher atomization temperatures. Further, the presence of sulfate can suppress lead absorbance, thereby requiring the use of a lanthanum-releasing agent.

There is a long felt need in the art for rapid, simple detection of lead in samples such as drinking water, plant, and water treatment effluent, hazard waste sites, streams, estuaries and coastal waters. The present invention satisfies this need.

BRIEF SUMMARY OF THE INVENTION

Work with surfactants, and solid and soluble polymers has shown that we can generate and maintain hydrophobic non-aqueous domains even in pure water. By solubilizing the bromide anion in these domains we have found it possible to extract the lead into the hydrophobic domain, create the cluster, and get efficient luminescence even in water. We have also found that by using a tetraalkyl ammonium salt dissolved in an appropriate water immiscible nonaqueous solvent, we can extract the lead from the aqueous phase and create a sufficiently dry environment for the cluster that it can emit efficiently.

It is one object of the invention to create copolymers with interfaces at which lead can form clusters exhibiting luminescent properties. It is another object of the invention to create a cross-linked polymer with similar interfaces. It is also an object of the invention to optimize the detection limit of the lead detection system on a solid support, while harming the environment as little as possible.

The present invention provides compositions and methods useful for fast, inexpensive, and sensitive measurements of lead without the use of bulky instrumentation, which is ideal for on-site analysis.

In one embodiment, the invention provides compositions and methods for extracting or isolating lead dissolved in water, forming a luminescent cluster, and qualitatively or quantitatively determining the lead concentration from the ultraviolet excited luminescence of the cluster. A high concentration of bromide is used to assist formation of the lead clusters $(Pb_4Br_{11})^{3-}$. A polymer, block copolymer, surfactant, or water immiscible extraction solvent can be used to isolate the cluster in a domain suitable for luminescence. A hydrophobic cation is used with the bromide salt to solubilize the cluster in the nonaqueous domain and further protect the cluster from interaction with water. Suitable salts are tetrabutylammonium bromide (TBAB) and tetraoctylammonium bromide (TOAB). TOAB has proved to be a superior source of bromide, probably because of its greater hydrophobicity and larger size, which enhance transfer into the hydrophobic domain and increase shielding. The polymer can be a homo or hetero polymer or linear or crosslinked polymer. A surfactant, such as cetyltrimethylammonium bromide (CTAB), may be used either by itself or in conjunction with a polymer to enhance the hydrophobic domains. Excess sodium bromide may be added to the aqueous phase to enhance cluster formation. In the two-phase solvent extraction system (e.g., toluene, xylene, cyclohexane), the hydrophobic bromide is dissolved directly in the solvent. In systems where a water-soluble polymer and/or surfactant are used, the tetraalkylammonium bromide is dissolved in the surfactant micelles or hydrophobic domains in the polymer. For insoluble polymer, the tetraalkylammonium bromide is dissolved and dispersed in the polymer film. Water-miscible solvents may be added to improve cluster formation, luminescence, or separation into the desired domain or solvent.

Copolymer synthesis comprises radical polymerization, including radical initiator (i.e., AIBN), bulk polymerization, monomers, and a cross-linker. Radical polymerization of the invention can be characterized in one aspect by the following formula:

The system can be excited with near ultraviolet radiation (330-390 nm) and the green luminescence intensity of the cluster can then be measured with a detector such as a photodiode or a photomultiplier tube. The ultraviolet radiation can be emitted from a source, including, but not limited to, an ultraviolet LED, laser diode, fluorescent screen, incandescent bulb, and an arc lamp. In one aspect, the arc lamp is a filtered mercury arc lamp. From a calibration curve of emission intensity versus lead concentration, the concentration is then determined. In the separated phase system, excitation need only be in the phase containing lead.

In one embodiment, all polymers are cast during the same day.

In another embodiment, polymers are submerged in lead solution for about 20 minutes.

In yet another embodiment, the invention provides compositions and methods to determine the structure of compounds such as a $Pb_4Br_{11}^{3-}$ cluster.

Various aspects and embodiments of the invention are described in further detail below. Many of the known techniques are not described herein, but can be found in, inter alia, Clarke et al., 2000, Anal. Chem., 72:3468-3475, Price et al., Anal. Chem., 1998, 70:265-270, Dutta et al., 2004, Spectrochimica Acta Part A, 60:1447-1451, Singh et al., 2004, Inorganica Chimica Acta, 357:1589-1592, Jones et al., 1982, Polyhedron, 1:2:169-174, Dutta et al., 2002, Inorg. Chem., 41:6938-6940, Gomis et al., 1985, Talanta, 32:9:915-920, Weber et al., 1975, Croatica Chemica Acta, 47:1:51-58, Gruijter, J. Solid State Chem., 6:151-162, and U.S. Pat. Nos. 5,100,951 and 5,019,516.

One of ordinary skill in the art will also appreciate that other solvents, polymers, and alkylammonium salt are all variables that are encompassed within the invention. While block copolymers are disclosed herein, one of ordinary skill in the art will appreciate that further modifications and combinations are within the scope of the invention to find homogeneous systems either as pure block or water-soluble copolymers alone or with surfactants. The AOT system or other surfactants suitable for forming reverse micelles promise a useful homogeneous system.

Various aspects and embodiments of the invention are described in further detail below.

BRIEF DESCRIPTION OF THE DRAWINGS

FIG. 6 represents a graphic analysis depicting the fluorescence spectra of polymer at varying lead concentrations. The ordinate represents "Intensity," in cps. The abscissa represents wavelength in nm. The groups are control (closed black diamond (cps); 10 microM (closed square); 35 microM (closed light gray triangle); 150 microM (light gray x); and 230 microM (dark x with a vertical line).

DETAILED DESCRIPTION OF THE INVENTION

Definitions and Abbreviations

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The phrase "aqueous sample" refers to any kind of sample which is primarily water, i.e., at least 50% water.

"AOT" refers to sodium bis-(2-ethylhexyl)sulfosuccinate.

"CTAB" refers to cetyltrimethylammonium bromide.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker.

"Luminescent lead cluster" or "lead cluster" refers to the complex $(Pb_4Br_{11})^{3-}$ or similar cluster structures that may exist in solution.

"Nonaqueous phase" includes, but is not limited to, organic substances such as toluene, hydrophobic domains formed by the micelles of surfactants, the hydrophobic domains of water-miscible polymers, and the hydrophobic domains of water insoluble but swellable polymers.

"Phase transfer catalyst" includes but is not limited to quaternary ammonium ions.

"Reverse micelle surfactant" includes but is not limited to AOT.

"TBAB" refers to tetrabutylammonium bromide.

"TOAB" refers to tetraoctylammonium bromide.

A "sample," as used herein, refers preferably to a sample of interest, including, but not limited to, water, and other materials. A sample can also be any other source of material obtained from a source which may contain lead.

"Solvent" includes, but is not limited to, toluene.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

"Surfactant" includes, but is not limited to, CTAB.

"Water" includes, but is not limited to, drinking water, plant, and water treatment effluent, hazard waste sites, streams, estuaries and coastal waters and other aqueous media.

EMBODIMENTS

In one embodiment, the invention provides a method for measuring lead from an aqueous environment. Three types of monitoring systems have been described herein and are encompassed within the present invention. In the first system, the lead is extracted into a nonaqueous phase where it forms the luminescent lead cluster, but excellent detection still results even when the solvent is saturated and still in contact with water.

In the second system, the hydrophobic domain was introduced directly into the water in a soluble form. This allows a one-phase measurement.

In the third system, the hydrophobic domain was in a water-insoluble but swellable polymer. With a suitably reversible system, real time monitoring of the lead concentration should be feasible. The current irreversible system would be good for catching the highest lead concentration during the sampling interval.

The present invention provides detection limits of the two-phase system which are below the current EPA action limit. The homogeneous system detection is above the EPA limit, and the solid polymer system is well above it. However, being able to measure high levels in waste sites would still be useful for following remediation.

One of ordinary skill in the art will understand that the ratios of the various monomers and polymers can be varied. For example, ratios of 1:1 and 1:2 styrene:N,N'-dimethylacrylamide can be used. Additionally, N,N'-dimethylacrylamide can be used alone. Also included herein is a ratio of 2:1 N,N'-dimethylacrylamide:methacrylamide. Crosslinked polymers useful in the invention include 2:1 N,N'-dimethylacrylamide:styrene, with about 3-5% N,N'-methylene-bis-acrylamide crosslinker. Characterization can be by solid state NMR analysis to detect, inter alia, monomer rations.

Also encompassed within the invention are bromine salts with hydrophobic domains which can penetrate polymers, such as tetrabutylammonium bromide (TBAB) and tetraoctylammonium bromide (TOAB). Sample preparation includes: cast polymer in a support mesh (black was used herein to minimize interference); submerge polymers in lead solution for 10 minutes; allow polymers to dry for 12 hours; take fluorescence spectrum using fluorimeter. Characterization can be by, inter alia, UV-VIS spectroscopy (i.e., absorption spectrum) and luminescence spectroscopy (i.e., excitation and emission spectra). The methods of the present invention show that upon synthesis of polymers the organic layer of water soluble polymer exhibits luminescence in the presence of lead, but there is no luminescence in the absence of $Pb^{2+}$; that 1:2 weight ratio of styrene:N,N'-diemthylacrylamide exhibits luminescence, but that there is no luminescence in the absence of $Pb^{2+}$.

A sample of potable water to be tested in accordance with the present invention can be collected in accordance with conventional sampling techniques. The size of the sample may vary. Generally speaking, a 100 milliliter sample of potable water is sufficient for the technique of this invention. In one aspect, about 50 milliliters can be sampled. In yet another aspect, about 10 milliliters can be sampled. In a further aspect, about 1 milliliter of water can be sampled. One of ordinary skill in the art will appreciate that standard samples can be prepared using water with known amounts of lead added. Such standard samples can be processed in a manner identical to a test sample and the results compared, or used for instrument calibration.

Luminescence intensity can be measured using various techniques known in the art, including, but not limited to, using a detector such as a photodiode, phototransistor, avalanche photodiode, photoresistor, and a photomultiplier tube.

Various analytical techniques not described herein, are known in the art, and are encompassed within the methods of the invention. It is also possible to use known titration techniques to analytically determine the amount of lead in the sample. Another known analytical technique which may be used is the inductively coupled plasma technique. Such techniques known in the art are described in: U.S. Pat. Nos. 5,019,516, 5,100,951; Juan D'iaz-Garc'ia, Analytica Chimica Acta 486 (2003) 1-10; and Worsfold et al., Journal of Automated Methods & Management in Chemistry Vol. 24, No. 2, pp. 41-47.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

Example 1

Two Phase System (Toluene)

Methods

Figure 1:
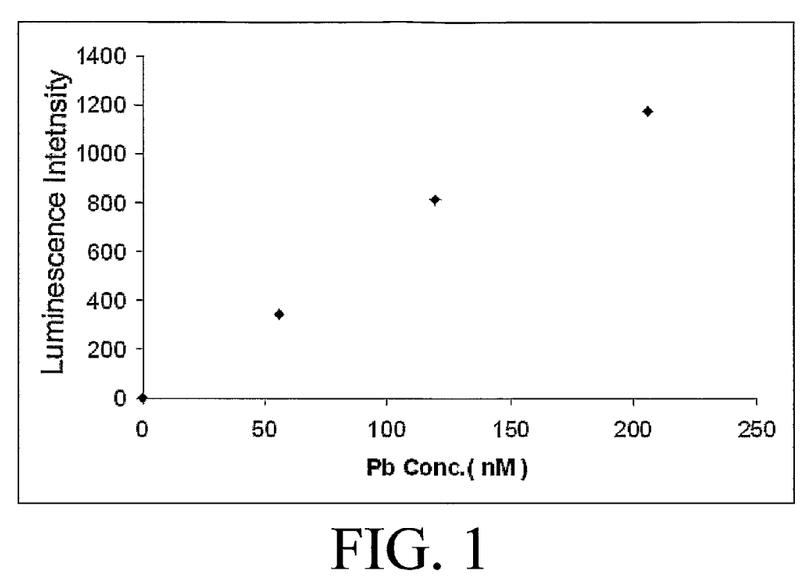
FIG. 1 graphically represents the plot of luminescence intensity of the lead cluster versus lead concentration. The ordinate is the luminescence intensity. The abscissa is the concentration of lead in nanomolar. The lead was extracted from water into toluene contain 0.1M TOAB. The plot is linear up to at least 50 μM.

The lowest detection limits have been achieved using a two-phase system consisting of TOAB in toluene to extract the complex into the toluene. The partitioning of the complex into the toluene layer is highly favored so that the volume of toluene can be smaller than the water volume, which further improves the detection limits. Sodium bromide (1 M) can be added to the aqueous phase to improve the detection limit, but is not required. A water sample to be analyzed was placed in a long cell. The toluene and TOAB along with NaBr were added. The solution is shaken or mixed and then allowed to phase separate. The upper toluene layer was then placed in the luminescence detection instrument, excited in the 350-380 nm region, and the emission intensity was monitored at approximately 550 nm (the optimum wavelength varies with solvent). FIG. 1 shows a calibration curve for the system at low levels; less than 50 nM lead was detected.

Results

The detection limit was estimated to be below 25 nM. The EPA action level is 72 nM. (See FIG. 1)

Example 2

Two Phase System (Cyclohexane)

Cyclohexane was used as an immiscible phase. This method yielded a diffuse, thin, highly luminescent layer in the cycloxane layer. (This highly luminescent layer might well have allowed even lower detection limits.)

Example 3

Surfactant System

Figure 2:
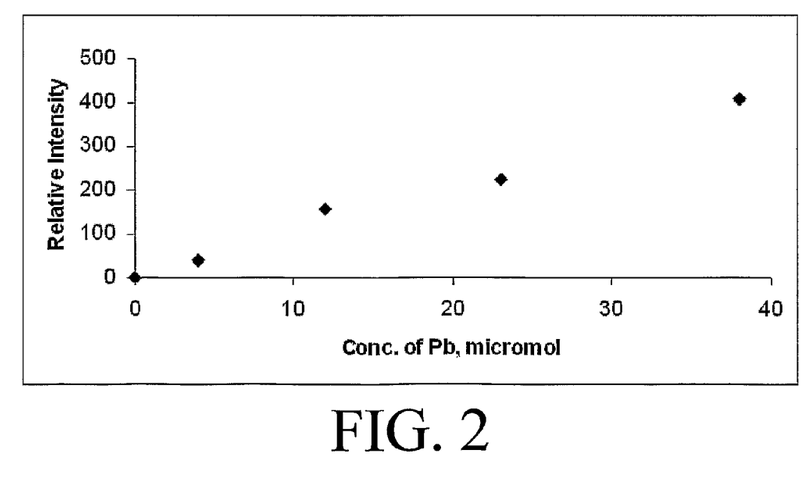
FIG. 2 graphically represents the luminescence intensity of the lead cluster versus lead concentration in the water with an added surfactant. The ordinate is the relative intensity of the luminescence. The abscissa is the concentration of lead in micromolar. The aqueous solution was saturated with CTAB. The mixture was 3 volumes of the lead-containing aqueous phase with 2 volumes of 0.2 M TOAB in acetonitrile. A homogeneous solution resulted FIG. 3 graphically represents the emission of lead cluster in TOAB doped solid copolymer in water. The ordinate is the emission intensity. The abscissa is the emission wavelength in nanometers. The aqueous lead concentration was 1 mM.

The detection capabilities of a surfactant-based system are shown in FIG. 2. The solution contained acetonitrile to solubilize the TOAB and was saturated with CTAB to form protective micelles. The detection limits were about 1 μM, but no optimization had been performed.

Example 4

Water Insoluble (but Swellable) Polymer

Figure 3:
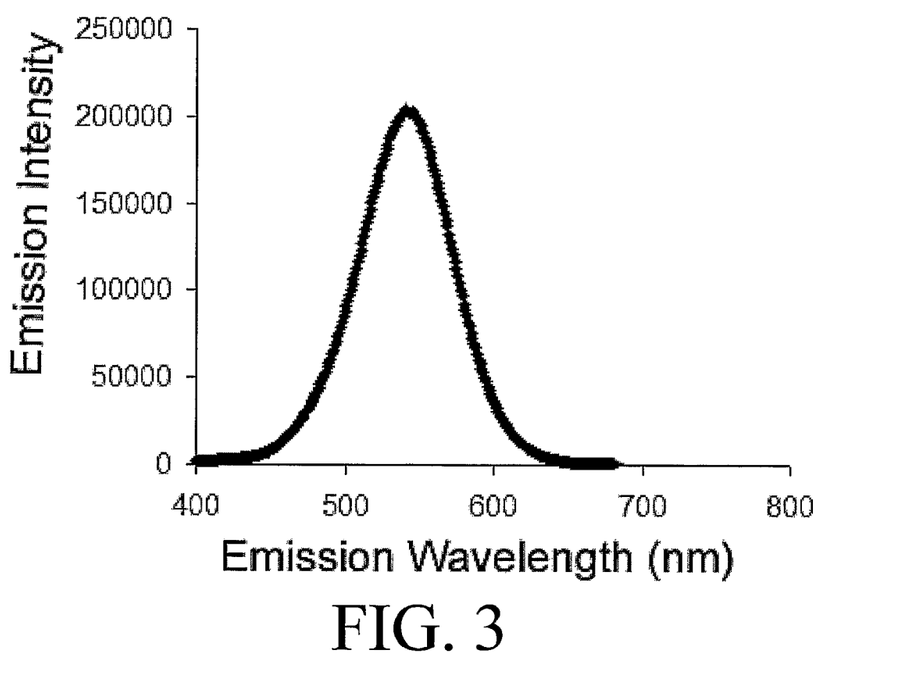

FIG. 3 shows the luminescence of a polymer film immersed in a 1 mm lead solution. The polymer was a copolymer of N,N-dimethylacrylamide and poly(ethylene glycol) methyl ether methacrylate and and a hydrophobic crosslinker which supplied both aqueous and hydrophobic domains. The copolymer was doped with TOAB in acetonitrile and then dried before use. This polymer is sufficiently hydrophilic to swell readily in water, which allowed easy entry of the aqueous lead which could then readily react with the TOAB to form the cluster. The emission of the film was in water and was fully swollen. This demonstrates that excellent protection of, and formation of, the cluster can be achieved even from a pure water sample.

Figure 4:
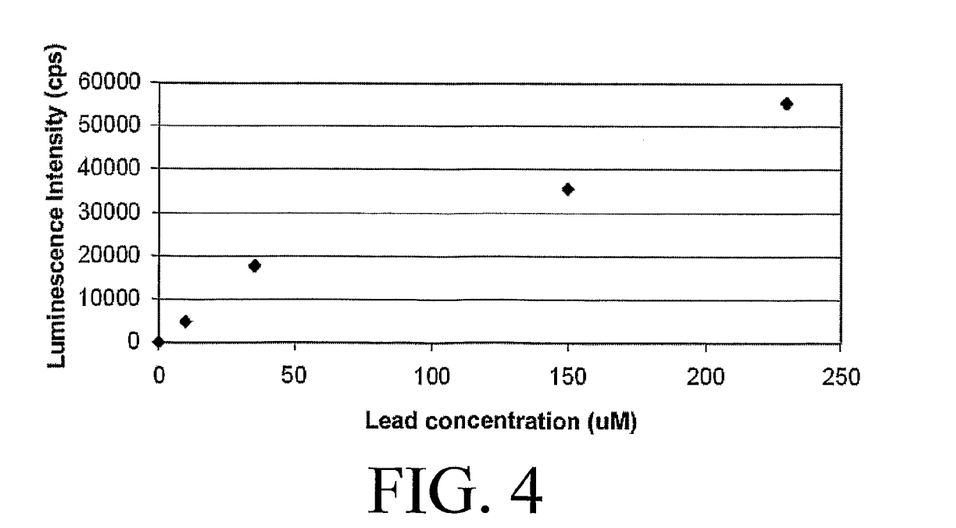
FIG. 4 graphically represents the luminescence intensity of a lead cluster versus initial aqueous lead concentration in a water swollen TOAB copolymer described in the text. The ordinate is the luminescence intensity. The abscissa is the lead concentration in (uM). The monomers were polymerized on a fine black cloth mesh to give them better physical properties. The sample was air dried before making the measurement. Even without drying, the emission was still bright enough to detect visually.

A detection limit below 10 μM was achieved using a water-insoluble but swellable polymer made from styrene and dimethylacrylamide. The data for this are shown in FIG. 4. The blank limits the detection limit here, but this can certainly be improved on.

The solid polymer films are not readily reversible. Further, the emission is significantly brighter dry than wet. However, this makes an ideal detector for taking samples in the field, bringing the films back, drying them, and then measuring the emission intensity to determine the lead concentration. The dry film could then be kept as a permanent record. A suitable polymer can probably be made completely irreversible. This could allow leaving a film in place for a period and then reading it out to determine the maximum lead level at that location during the test period. This would be useful to determine if unacceptable excursions occurred during the sampling without having to do continuous monitoring.

Example 5

Alternative Surfactant System (AOT)

An alternative surfactant system is to use sodium bis-(2-ethylhexyl)sulfosuccinate (AOT). AOT in hydrophobic solvent such as oil allows dissolving large quantities of water without phase separation (reverse micelles or microemulsion). These inverted micelles are micro pockets of water surrounding by AOT dispersed in the bulk hydrophobic solvent. The hydrophobic solvent could be used to dissolve the TOAB. The water to be analyzed would be added directly to this and mixed. The lead chloro cluster also causes emission, but less so that the bromo complex. By replacing the tetraalkyl bromide with the corresponding chloride, an analogous procedure could be used, but with lower sensitivity.

Example 6

Further Polymer Characterization

Figure 5:
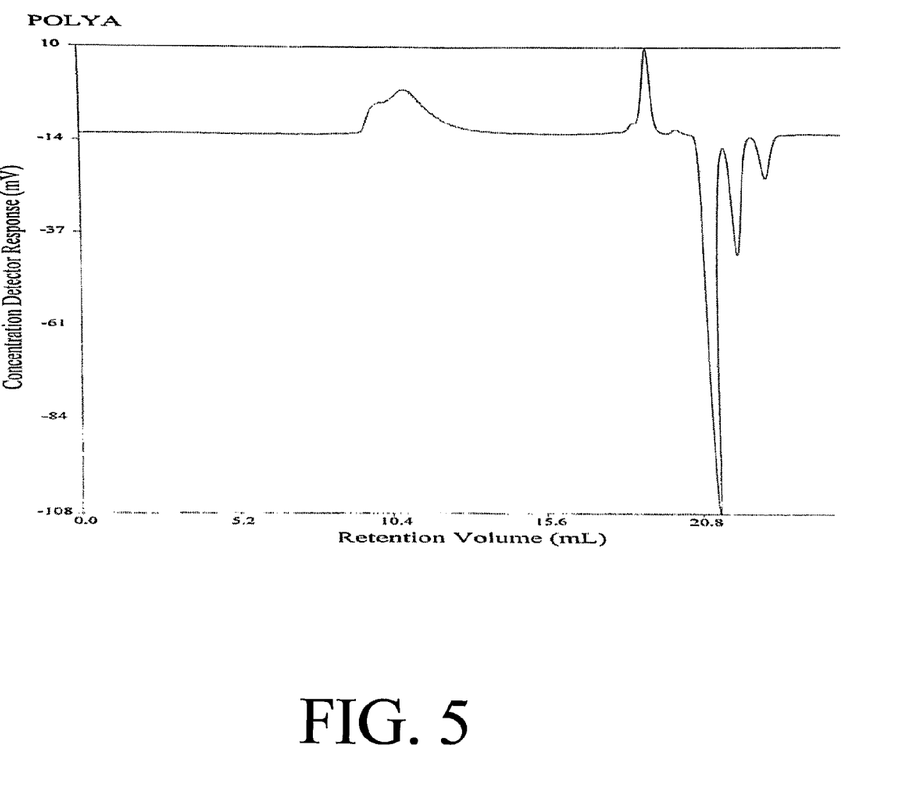
FIG. 5 represents a spectrum summarizing GPC data of 1:2 styrene:N,N'-dimethylacrylamide polymer (M.W.=80,000 g/mole; PDI=2.4). The ordinate represents the concentration detector response (mV) and the abscissa represents retention volume in ml.
Figure 6:
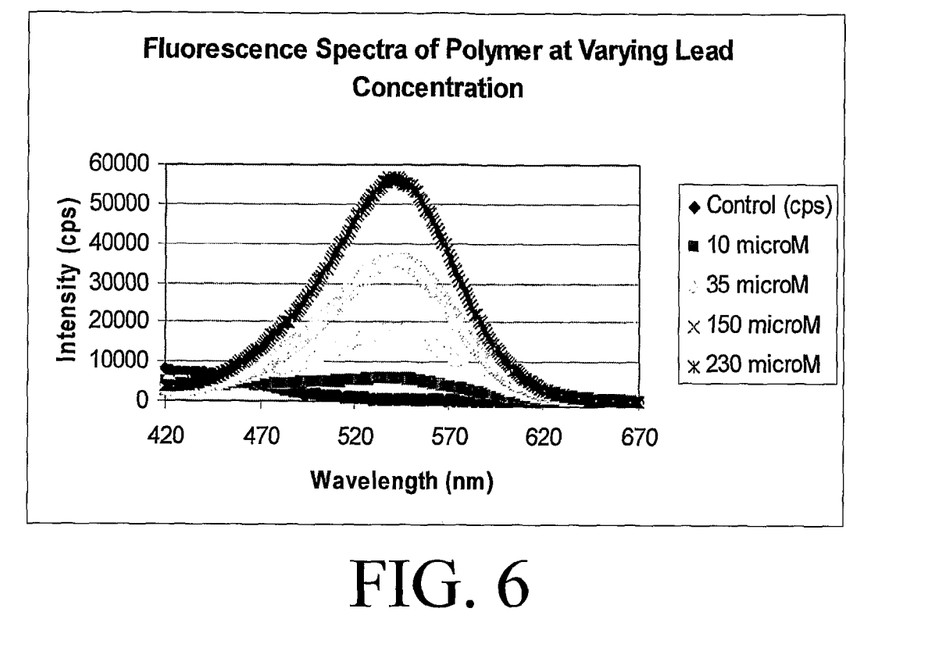
Figure 7:
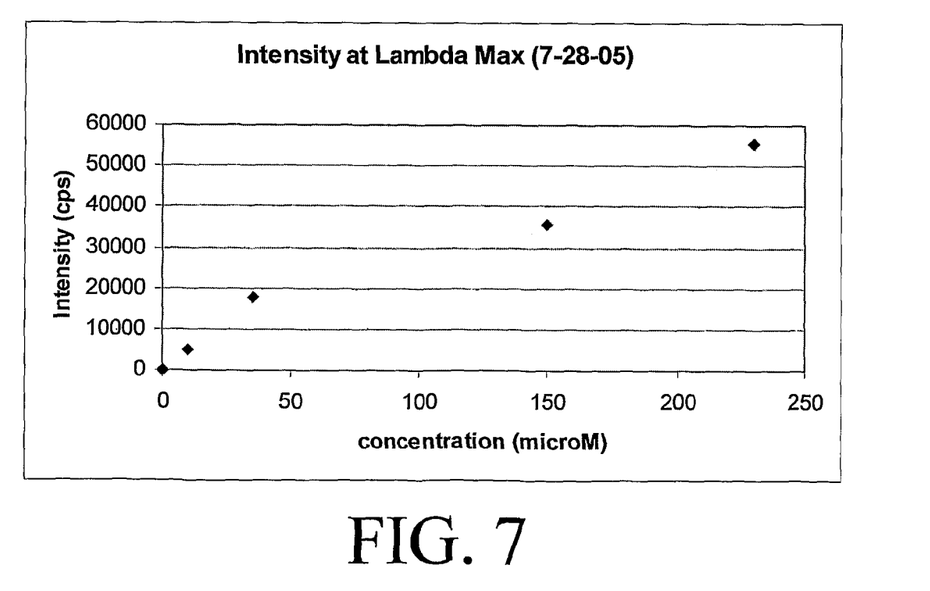
FIG. 7 represents a graphic analysis of intensity (550 nm) at the emission maximum. The ordinate represents intensity in cps and the abscissa represents concentration in μM.

FIG. 5 provides a spectrum summarizing GPC data of 1:2 styrene:N,N'-dimethylacrylamide polymer (M.W.=80,000 g/mole; PDI=2.4). FIG. 6 represents a graphic analysis depicting the fluorescence spectra of this polymer at varying lead concentrations. FIG. 7 represents a graphic analysis of intensity at the emission maximum.

CONCLUSIONS

The lead chloro cluster is also emissive, but less so than the bromo complex. By replacing the tetraalkyl bromide with the corresponding chloride, an analogous procedure could be used, but with lower sensitivity.

We have successfully demonstrated three types of monitoring systems. In the first, the lead is extracted into an a nonaqueous phase where it forms the luminescent lead cluster, but excellent detection still results even when the solvent is saturated and still in contact with water.

In the second system, we introduce the hydrophobic domain directly into the water in a soluble form. This allows a one-phase measurement.

In the third, the hydrophobic domain is in an insoluble water-swellable polymer. With a suitably reversible system, real time monitoring of the lead concentration should be feasible. The current irreversible system would be good for catching the highest lead concentration during the sampling interval.

The detection limits of the two-phase system are below the current EPA action limit. The homogeneous system exceeds the limit, and the solid polymer system is well above it. However, being able to measure high levels in waste sites would still be useful for following remediation.

The disclosures of each and every patent, patent application, and publication cited herein are hereby incorporated by reference herein in their entirety. One of skill in the art will appreciate that the superiority of the compositions and methods of the invention relative to the compositions and methods of the prior art are unrelated to the physiological accuracy of the theory explaining the superior results.

Headings are included herein for reference and to aid in locating certain sections. These headings are not intended to limit the scope of the concepts described therein under, and these concepts may have applicability in other sections throughout the entire specification.

Other methods which were used but not described herein are well known and within the competence of one of ordinary skill in the art of chemical and instrumentation techniques.

The description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Accordingly, the present invention is not intended to be limited to the embodiments shown herein but is to be accorded the widest scope consistent with the principles and novel features disclosed herein.

What is claimed is:

1. A method for measuring the amount of lead in an aqueous sample, said method comprising obtaining an aqueous sample, extracting said lead from said sample, wherein the lead is extracted via a phase transfer catalyst into a nonaqueous phase, wherein said nonaqueous phase comprises copolymers with interfaces at which lead forms clusters with luminescent properties, further wherein said extracted lead forms a luminescent lead cluster, inducing luminescence of said lead cluster, and measuring the amount of said luminescence.

2. The method of claim 1, wherein the formation of said luminescent lead cluster is enhanced with sodium bromide.

3. The method of claim 1, wherein the nonaqueous phase comprises a surfactant, solvent, or water miscible polymer.

4. The method of claim 1, wherein the nonaqueous phase has been introduced directly into the sample in a soluble form.

5. The method of claim 1, wherein the nonaqueous phase comprises a reverse surfactant.

6. The method of claim 1, wherein said sample is water.

7. The method of claim 1, wherein said lead cluster is induced to luminesce with ultraviolet light.

8. A method for measuring the amount of lead in an aqueous sample, said method comprising obtaining an aqueous sample, extracting said lead from said sample, wherein the lead is extracted via a phase transfer catalyst into a nonaqueous phase, wherein said nonaqueous phase comprises a cross-linked polymer with interfaces at which lead forms clusters with luminescent properties, further wherein the clusters are extracted into the polymer, further wherein said extracted lead forms a luminescent lead cluster, inducing luminescence of said lead cluster, and measuring the amount of said luminescence.

9. The method of claim 8, wherein the formation of said luminescent lead cluster is enhanced with sodium bromide.

10. The method of claim 8, wherein the nonaqueous phase comprises a surfactant, solvent, or water miscible polymer.

11. The method of claim 8, wherein the nonaqueous phase has been introduced directly into the sample in a soluble form.

12. The method of claim 8, wherein the nonaqueous phase comprises a reverse surfactant.

13. The method of claim 8, wherein said sample is water.

14. The method of claim 8, wherein said lead cluster is induced to luminesce with ultraviolet light.

* * * * *